(12) United States Patent
Wang et al.

(10) Patent No.: US 10,202,403 B2
(45) Date of Patent: Feb. 12, 2019

(54) MACROCYCLIC BENZOFURAN COMPOUNDS FOR THE TREATMENT OF HEPATITIS C

(71) Applicant: BRISTOL-MYERS SQUIBB COMPANY, Princeton, NJ (US)

(72) Inventors: Tao Wang, Farmington, CT (US); Zhongxing Zhang, Madison, CT (US); John F. Kadow, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/515,170

(22) PCT Filed: Oct. 1, 2015

(86) PCT No.: PCT/US2015/053375
§ 371 (c)(1),
(2) Date: Mar. 29, 2017

(87) PCT Pub. No.: WO2016/054299
PCT Pub. Date: Apr. 7, 2016

(65) Prior Publication Data
US 2017/0217989 A1  Aug. 3, 2017

Related U.S. Application Data

(60) Provisional application No. 62/058,836, filed on Oct. 2, 2014.

(51) Int. Cl.
  *C07D 498/22* (2006.01)
  *C07D 493/04* (2006.01)
  *C07D 493/14* (2006.01)
  *C07D 498/04* (2006.01)

(52) U.S. Cl.
  CPC ....... *C07D 498/22* (2013.01); *C07D 493/04* (2013.01); *C07D 493/14* (2013.01); *C07D 498/04* (2013.01)

(58) Field of Classification Search
  None
  See application file for complete search history.

(56) References Cited

FOREIGN PATENT DOCUMENTS

WO  WO 2008/125874     * 10/2008  ........... C07D 493/04
WO  WO 2008/125874 A1   10/2008

OTHER PUBLICATIONS

CAS RN 1072843-65-2 (entered into STN on Nov. 14, 2008) (Year: 2008).*

* cited by examiner

*Primary Examiner* — Craig D Ricci
(74) *Attorney, Agent, or Firm* — Elliott Korsen

(57) ABSTRACT

Compounds of formula I, including their salts, as well as compositions and methods of using the compounds are set forth. The compounds have activity against hepatitis C virus (HCV) and may be useful in treating those infected with HCV.

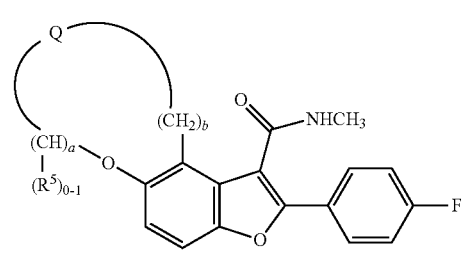

5 Claims, No Drawings

MACROCYCLIC BENZOFURAN COMPOUNDS FOR THE TREATMENT OF HEPATITIS C

CROSS-REFERENCE TO RELATED APPLICATIONS

This application claims priority to U.S. Provisional Application Ser. No. 62/058,836, filed Oct. 2, 2014; the entire content of which is incorporated herein reference.

FIELD OF THE INVENTION

The invention relates to novel compounds, including their salts, which have activity against hepatitis C virus (HCV) and which are useful in treating those infected with HCV. The invention also relates to compositions and methods of making and using these compounds.

BACKGROUND OF THE INVENTION

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. *N. Engl. J. Med.* 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., *Journal of Virology* 2002, 3482-3492; and Defrancesco and Rice, *Clinics in Liver Disease* 2003, 7, 211-242.

Currently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl. J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

HCV-796, an HCV NS5B inhibitor, has shown an ability to reduce HCV RNA levels in patients. The viral RNA levels decreased transiently and then rebounded during dosing when treatment was with the compound as a single agent but levels dropped more robustly when combined with the standard of care which is a form of interferon and ribavirin. The development of this compound was suspended due to hepatic toxicity observed during extended dosing of the combination regimens. U.S. Pat. No. 7,265,152 and the corresponding PCT patent application WO2004/041201 describe compounds of the HCV-796 class. Other compounds have been disclosed; see for example, WO2009/101022, as well as WO 2012/058125.

What is therefore needed in the art are additional compounds which are novel and effective against hepatitis C. Additionally, these compounds should provide advantages for pharmaceutical uses, for example, with regard to one or more of their mechanism of action, binding, inhibition efficacy, target selectivity, solubility, safety profiles, or bioavailability. Also needed are new formulations and methods of treatment which utilize these compounds.

SUMMARY OF THE INVENTION

There are disclosed compounds of formula I, including pharmaceutically acceptable salts thereof

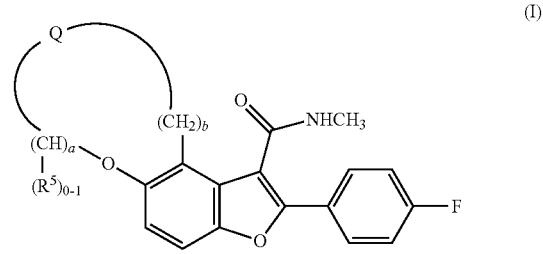

wherein
a is 1, 2, 3, 4, 5, or 6;
b is 1, 2, 3, 4, 5, or 6;
$R^5$ is H, $C_1$-$C_6$ alkyl or $C_1$-$C_6$ alkenyl;
Q is
   a) -absent;
   b) —CH═CH—;

c) —(Ar$_1$)$_e$— wherein Ar$_1$ is phenyl, biphenyl or naphthyl and c is 1 or 2;
d) —(CH$_2$O)$_d$—; wherein d is 1 or 2

e)

wherein R$^7$ is SO2-optionally substituted aryl;

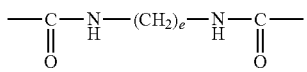
f)

and e is 1, 2 or 3;
g) —X$_1$—(CH$_2$)$_f$—Ar$_2$—(OCH$_2$)$_g$—X$_2$,
wherein f is 1, 2 or 3, g is 1 or 2 and X$_1$ and X$_2$ are independently selected from
aryl,

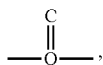

—O—, or C$_3$-C$_6$ cycloalkyl;
Ar$_2$ is

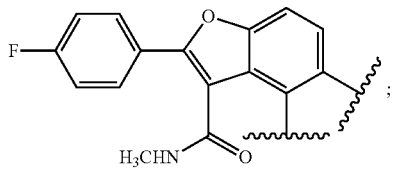

or a pharmaceutically acceptable salt thereof.

The invention also relates to pharmaceutical compositions comprising a compound of formula 1, including a pharmaceutically acceptable salt thereof, and a pharmaceutically acceptable carrier.

In addition, the invention provides one or more methods of treating hepatitis C infection comprising administering a therapeutically effective amount of a compound of formula I to a patient.

Also provided as part of the invention are one or more methods for making the compounds of formula I.

The present invention is directed to these, as well as other important ends, hereinafter described.

DETAILED DESCRIPTION OF THE EMBODIMENTS

Unless otherwise specifically set forth elsewhere in the application, the following terms may be used herein and shall have the following meanings: "Hydrogen" or "H" refers to hydrogen, including its isotopes, such as deuterium. "Halo" means fluoro, chloro, bromo, or iodo. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Halo" includes all halogenated isomers from monohalo substituted to perhalo substituted in substituents defined with halo, for example, "Haloalkyl" and "haloalkoxy", "halophenyl", "halophenoxy." "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic or non-aromatic carbocyclic ring. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Parenthetic and multiparenthetic terms are intended to clarify bonding relationships to those skilled in the art. For example, a term such as ((R)alkyl) means an alkyl substituent further substituted with the substituent R. Substituents which are illustrated by chemical drawing to bond at variable positions on a multiple ring system (for example a bicyclic ring system) are intended to bond to the ring where they are drawn to append.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, camsylate, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms. The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

As set forth above, the invention is directed to one or more compounds of formula I, including pharmaceutically acceptable salts thereof:

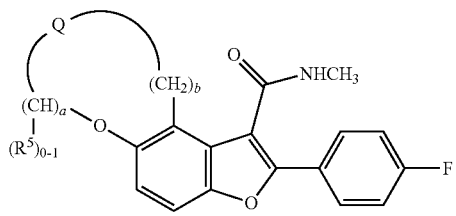

(I)

wherein
a is 1, 2, 3, 4, 5, or 6;
b is 1, 2, 3, 4, 5, or 6;
$R^5$ is H, $C_1$-$C_6$ alkyl or $C_1$-$C_6$ alkenyl;
Q is
  a) -absent;
  b) —CH=CH—;
  c) —$(Ar_1)_e$— wherein $Ar_1$ is phenyl, biphenyl or naphthyl and c is 1 or 2;
  d) —$(CH_2O)_d$—; wherein d is 1 or 2

 e)

wherein $R^7$ is SO2-optionally substituted aryl;

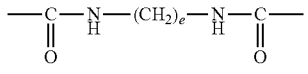 f)

and e is 1, 2 or 3;
  g) —$X_1$—$(CH_2)_f$—$Ar_2$—$(OCH_2)_g$—$X_2$,
    wherein f is 1, 2 or 3, g is 1 or 2 and $X_1$ and $X_2$ are independently selected from
    aryl,

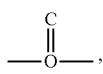

—O—, or $C_3$-$C_6$ cycloalkyl;
$Ar_2$ is

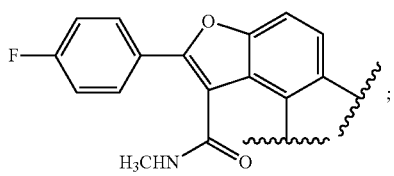

or a pharmaceutically acceptable salt thereof.
In another aspect of the invention, there are disclosed compounds of formula (I)

wherein
a is 1, 2, 3, 4, 5, or 6;
b is 1, 2, 3, 4, 5, or 6;
$R^5$ is $C_1$-$C_3$ alkenyl;
Q is
  a) -absent;
  b) —CH=CH—;
  c) —$(Ar_1)_e$— wherein $Ar_1$ is phenyl, biphenyl or naphthyl and c is 1 or 2;
  d) —$(CH_2O)_d$—; wherein d is 1 or 2

 e)

wherein $R^7$ is SO2-optionally substituted aryl;

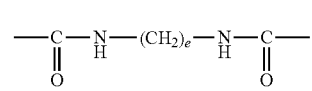 f)

and e is 1, 2 or 3;
  g) —$X_1$—$(CH_2)_f$—$Ar_2$—$(OCH_2)_g$—$X_2$,
    wherein f is 1, 2 or 3, g is 1 or 2 and $X_1$ and $X_2$ are independently selected from
    aryl,

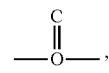

—O—, or $C_3$-$C_6$ cycloalkyl;
$Ar_2$ is

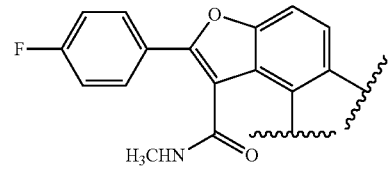

or a pharmaceutically acceptable salt thereof
In a further aspect of the invention, there are disclosed compounds of formula I
wherein
a is 1, 2, 3, 4, 5, or 6;
b is 1, 2, 3, 4, 5, or 6;
$R^5$ is —CH=$CH_2$;
Q is
  a) -absent;
  b) —CH=CH—;
  c) —$(Ar_1)_e$— wherein $Ar_1$ is phenyl, biphenyl or naphthyl and c is 1 or 2;
  d) —$(CH_2O)_d$—; wherein d is 1 or 2

 e)

wherein R[7] is SO2-optionally substituted aryl;
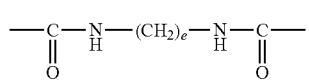 f)
and e is 1, 2 or 3;
g) —X$_1$—(CH$_2$)$_f$—Ar$_2$—(OCH$_2$)$_g$—X$_2$,
wherein f is 1, 2 or 3, g is 1 or 2 and X$_1$ and X$_2$ are independently selected from aryl,
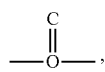
—O—, or cyclopropyl;
Ar$_2$ is
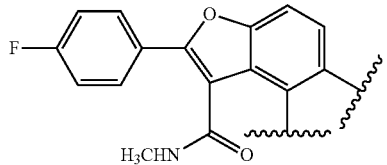
or a pharmaceutically acceptable salt thereof.
In a further aspect of the invention, there are disclosed the following compounds of the invention:
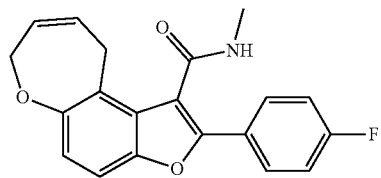
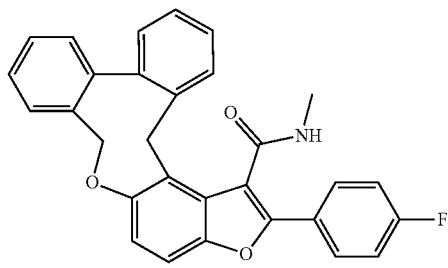
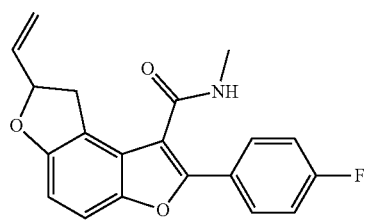
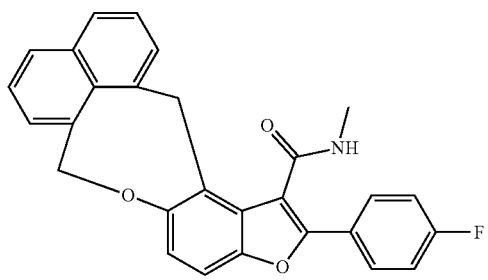
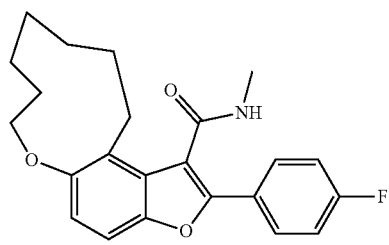
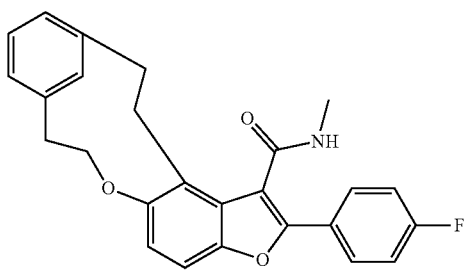
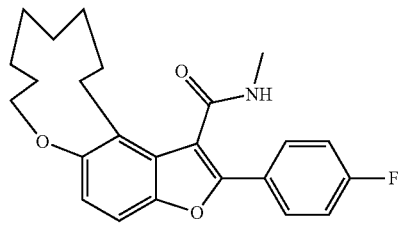
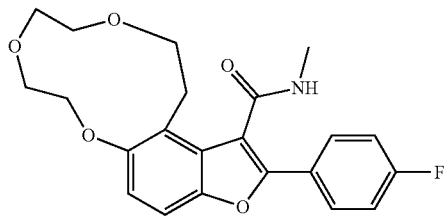

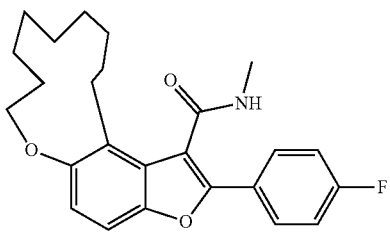
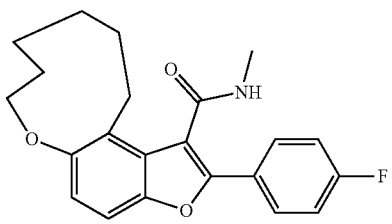
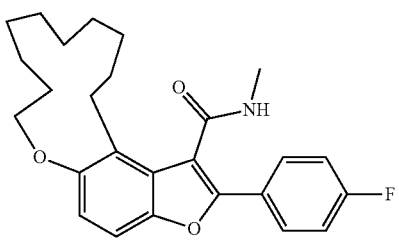
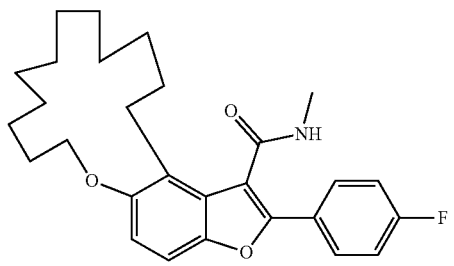
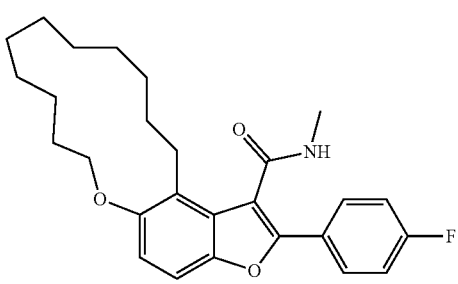
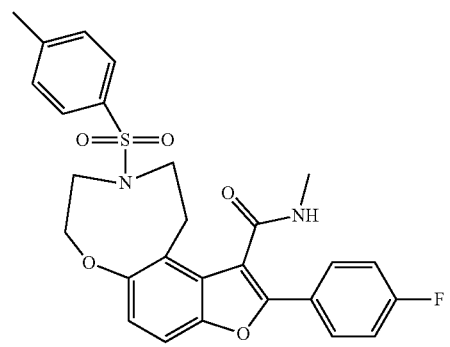
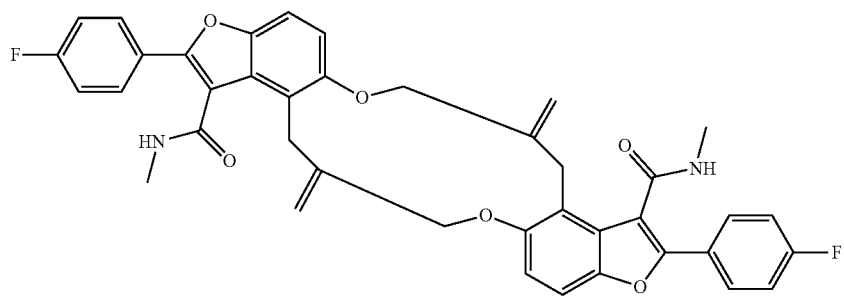
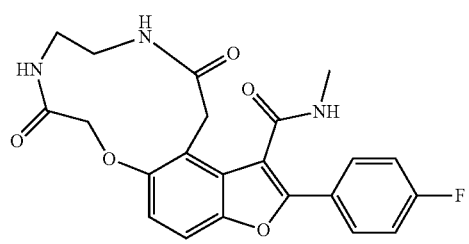
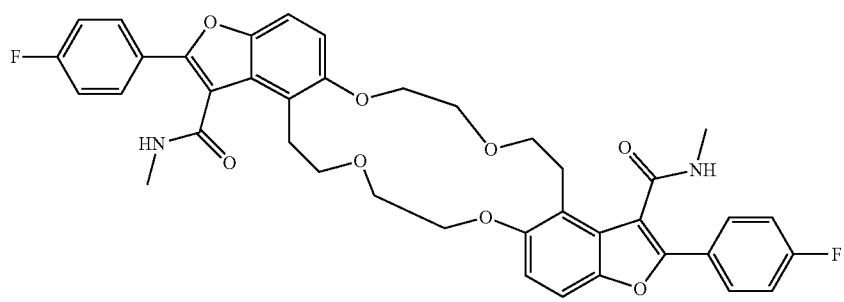

-continued

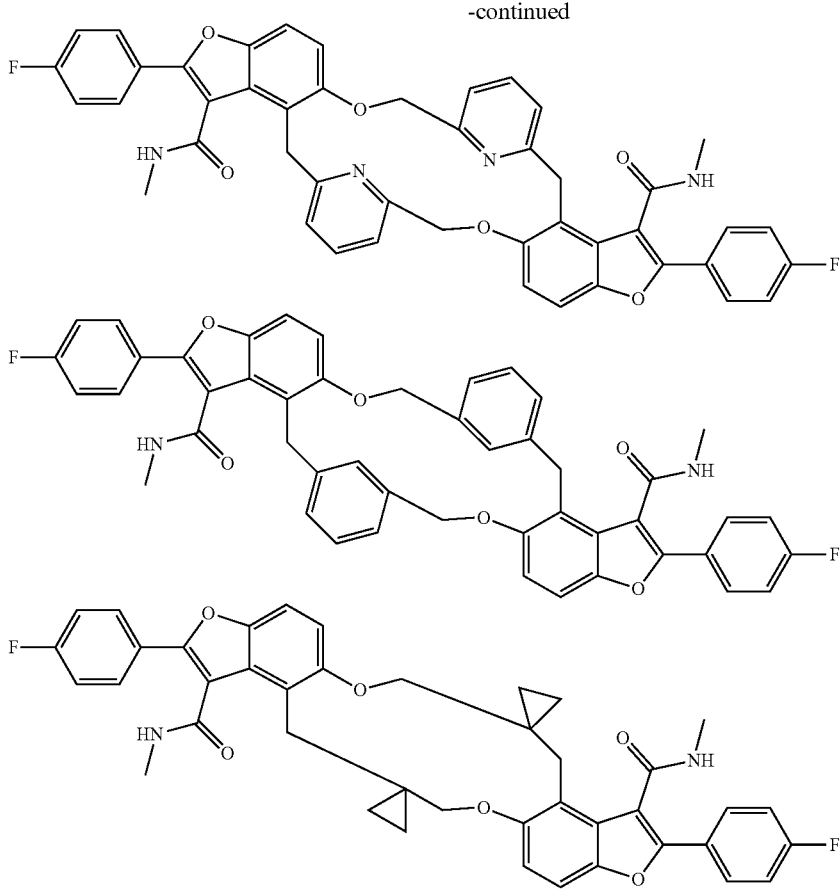

or a pharmaceutically acceptable salt thereof.

Pharmaceutical Compositions and Methods of Treatment

The compounds according to the various embodiments herein set forth demonstrate activity against HCV NS5B, and can be useful in treating HCV and HCV infection. Therefore, another aspect of the invention is a composition comprising a compound of formula I, or a pharmaceutically acceptable salt thereof, and a pharmaceutically acceptable carrier.

Another aspect of the invention is a composition further comprising an additional compound having anti-HCV activity.

Another aspect of the invention is a composition where the compound having anti-HCV activity is an interferon or a ribavirin. Another aspect of the invention is wherein the interferon is selected from interferon alpha 2B, pegylated interferon alpha, consensus interferon, interferon alpha 2A, interferon lambda, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound of formula I, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound of formula I or a pharmaceutically acceptable salt thereof.

Another aspect of the invention is a method of inhibiting the function of the HCV NS5B protein comprising contacting the HCV NS5B protein with a compound of formula I or a pharmaceutically acceptable salt thereof.

Another aspect of the invention is a method of treating an HCV infection in a patient comprising administering to the patient a therapeutically effective amount of a compound of formula I or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound of formula I, or a pharmaceutically acceptable salt thereof, in conjunction with (prior to, after, or concurrently) another compound having anti-HCV activity.

Another aspect of the invention is the method wherein the other compound having anti-HCV activity is an interferon or a ribavirin.

Another aspect of the invention is the method where the interferon is selected from interferon alpha 2B, pegylated interferon alpha, consensus interferon, interferon alpha 2A, interferon lambda, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method wherein the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method wherein the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, lozenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regimen, however, will be determined by a physician using sound medical judgment.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regimen, however, will be determined by a physician using sound medical judgment.

Some examples of compounds suitable for compositions and methods are listed in Table 1.

TABLE 1

| Brand Name | Physiological Class | Type of Inhibitor or Target | Source Company |
|---|---|---|---|
| NIM811 | | Cyclophilin Inhibitor | Novartis |
| Zadaxin | | Immuno-modulator | Sciclone |
| Suvus | | Methylene blue | Bioenvision |
| Actilon (CPG10101) | | TLR9 agonist | Coley |
| Batabulin (T67) | Anticancer | β-tubulin inhibitor | Tularik Inc., South San Francisco, CA |
| ISIS 14803 | Antiviral | antisense | ISIS Pharmaceuticals Inc, Carlsbad, CA/Elan Phamaceuticals Inc., New York, NY |
| Summetrel | Antiviral | antiviral | Endo Pharmaceuticals Holdings Inc., Chadds Ford, PA |

TABLE 1-continued

| Brand Name | Physiological Class | Type of Inhibitor or Target | Source Company |
|---|---|---|---|
| GS-9132 (ACH-806) | Antiviral | HCV Inhibitor | Achillion/Gilead |
| Pyrazolopyrimidine compounds and salts From WO-2005047288 26 May 2005 | Antiviral | HCV Inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | monoclonal antibody | XTL Biopharmaceuticals Ltd., Rehovot, Israel |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B Replicase Inhibitor | Wyeth/Viropharma |
| NM-283 | Antiviral | NS5B Replicase Inhibitor | Idenix/Novartis |
| GL-59728 | Antiviral | NS5B Replicase Inhibitor | Gene Labs/ Novartis |
| GL-60667 | Antiviral | NS5B Replicase Inhibitor | Gene Labs/ Novartis |
| 2'C MeA | Antiviral | NS5B Replicase Inhibitor | Gilead |
| PSI 6130 | Antiviral | NS5B Replicase Inhibitor | Roche |
| R1626 | Antiviral | NS5B Replicase Inhibitor | Roche |
| 2'C Methyl adenosine | Antiviral | NS5B Replicase Inhibitor | Merck |
| JTK-003 | Antiviral | RdRp inhibitor | Japan Tobacco Inc., Tokyo, Japan |
| Levovirin | Antiviral | ribavirin | ICN Pharmaceuticals, Costa Mesa, CA |
| Ribavirin | Antiviral | ribavirin | Schering-Plough Corporation, Kenilworth, NJ |
| Viramidine | Antiviral | Ribavirin Prodrug | Ribapharm Inc., Costa Mesa, CA |
| Heptazyme | Antiviral | ribozyme | Ribozyme Pharmaceuticals Inc., Boulder, CO |
| BILN-2061 | Antiviral | serine protease inhibitor | Boehringer Ingelheim Pharma KG, Ingelheim, Germany |
| SCH 503034 | Antiviral | serine protease inhibitor | Schering Plough |
| Zadazim | Immune modulator | Immune modulator | SciClone Pharmaceuticals Inc., San Mateo, CA |
| Ceplene | Immunomodulator | immune modulator | Maxim Pharmaceuticals Inc., San Diego, CA |
| CellCept | Immunosuppressant | HCV IgG immuno-suppressant | F. Hoffmann-La Roche LTD, Basel, Switzerland |
| Civacir | Immunosuppressant | HCV IgG immuno-suppressant | Nabi Biopharmaceuticals Inc., Boca Raton, FL |
| Albuferon-α | Interferon | albumin IFN-α2b | Human Genome Sciences Inc., Rockville, MD |
| Infergen A | Interferon | IFN alfacon-1 | InterMune Pharmaceuticals Inc., Brisbane, CA |

TABLE 1-continued

| Brand Name | Physiological Class | Type of Inhibitor or Target | Source Company |
|---|---|---|---|
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon-β-1a | Serono |
| Multiferon | Interferon | Long lasting IFN | Viragen/ Valentis |
| Wellferon | Interferon | Lympho-blastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc., San Diego, CA |
| Pegasys and Ribavirin | Interferon | PEGylated IFN-α2a/ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/ Ribavirin | Interferon | PEGylated IFN-α2b/ribavirin | Schering-Plough Corporation, Kenilworth, NJ |
| IP-501 | Liver protection | antifibrotic | Indevus Pharmaceuticals Inc., Lexington, MA |
| PSI-7851 | Antiviral | Nucleoside Polymerase Inhibitor | Pharmasset, Princeton, NJ, USA |
| PSI-7977 | Antiviral | Nucleotide NS5B Polymerase Inhibitor | Pharmasset, Princeton, NJ, USA |
| VCH-759 | Antiviral | NS5B Polymerase Inhibitor | ViroChem Pharma |
| VCH-916 | Antiviral | NS5B Polymerase Inhibitor | ViroChem Pharma |
| GS-9190 | Antiviral | NS5B Polymerase Inhibitor | Gilead |
| Peg-interferon lambda | Antiviral | Interferon | ZymoGenetics/Bristol-Myers Squibb |

Synthetic Methods

The compounds may be made by methods known in the art, including those described below. Some reagents and intermediates are known in the art. Other reagents and intermediates can be made by methods known in the art using commercially available materials. The variables (e.g. numbered "R" substituents) used to describe the synthesis of the compounds are intended only to illustrate how to make and are not to be confused with variables used in the claims or in other sections of the specification. Abbreviations used within the schemes generally follow conventions used in the art.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et₂O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine.

For the section of compounds in the 0000 series all Liquid Chromatography (LC) data were recorded on a Shimadzu LC-10AS or LC-20AS liquid chromotograph using a SPD-10AV or SPD-20A UV-Vis detector and Mass Spectrometry (MS) data were determined with a Micromass Platform for LC in electrospray mode.

HPLC Method (i.e., Compound Isolation).

Compounds purified by preparative HPLC were diluted in methanol (1.2 mL) and purified using a Shimadzu LC-8A or LC-10A or Dionex APS-3000 or Waters Acquity™ automated preparative HPLC system.

EXAMPLES

Preparation of Compound 1001:

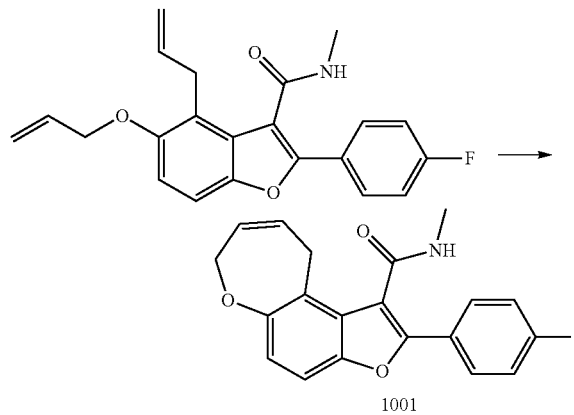

A mixture of 4-allyl-5-(allyloxy)-2-(4-fluorophenyl)-N-methylbenzofuran-3-carboxamide (10 mg) and Grubbs catalyst $2^{nd}$ generation (4.65 mg) in $CH_2Cl_2$ (20 mL) was heated to reflux for 3 hours. The solvent was removed under vacuum. The residue was purified by preparative HPLC system.

| 1001 | |
|---|---|
| MS (M − H)+ Calcd. | 338.1 |
| MS (M − H)+ Observ. | 338.5 |
| Retention Time | 1.65 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3u |

Preparation of Compounds 1002-1005:

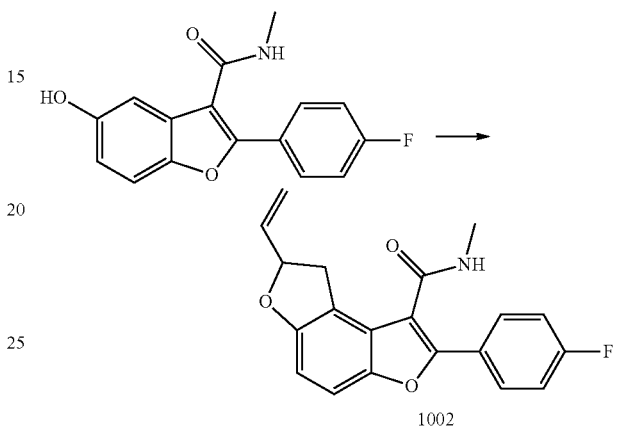

NaH (28.03 mg, 60%) was added into a solution of 2-(4-fluorophenyl)-5-hydroxy-N-methylbenzofuran-3-carboxamide (50 mg) and (E)-1,4-dibromobut-2-ene (75 mg) in PhH. The reaction was heated at 85° C. for 4-7 days. The reaction was quenched with MeOH and solvents were removed under vacuum to give a residue which was purified by preparative HPLC.

| 1002 | |
|---|---|
| MS (M + H)+ Calcd. | 338.1 |
| MS (M + H)+ Observ. | 338.1 |
| Retention Time | 2.08 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 1 mL/min |
| Wavelength | 220 |
| Solvent Pair | Water-Methanol-TFA |
| Column | PHENOMENEX-LUNA 2.0 × 30 mm 3 um |

Compounds 1003-1015 and 2001-2005 were prepared using the same procedure for compound 1002, using the corresponding di-electrophiles. LC condition for compounds 1003-1015 and 2001-2005 was the same as for compound 1002.

| Cmpd # | Di-Electrophile | Structure | MS (M + H)+ Calcd. | MS (M + H)+ Observ. | Retention Time (min) |
|---|---|---|---|---|---|
| 1003 | 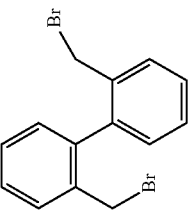 | 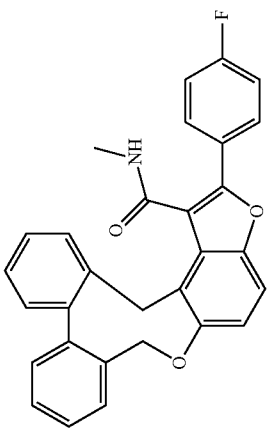 | 464.2 | 464.1 | 2.42 |
| 1004 | 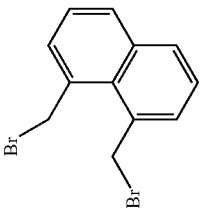 | 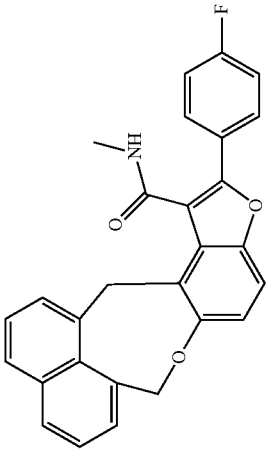 | 438.1 | 438.0 | 2.31 |
| 1005 | 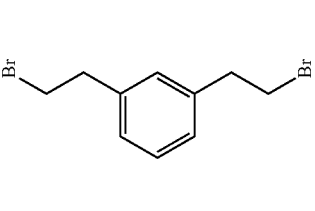 | 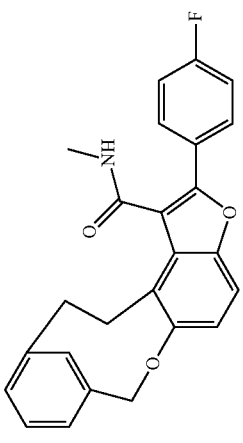 | 416.2 | 416.1 | 2.31 |

-continued

| Cmpd # | Di-Electrophile | Structure | MS (M + H)+ Calcd. | MS (M + H)+ Observ. | Retention Time (min) |
|---|---|---|---|---|---|
| 1006 | I~O~O~I | [structure with fluorophenyl benzofuran methylcarboxamide and dioxa macrocycle] | 400.2 | 400.1 | 2.15 |
| 1007 | I~~~~~I | [structure with fluorophenyl benzofuran methylcarboxamide and carbocyclic macrocycle] | 368.2 | 368.1 | 2.33 |
| 1008 | Br~~~~~Br | [structure with fluorophenyl benzofuran methylcarboxamide and oxa macrocycle] | 382.2 | 382.1 | 2.38 |
| 1009 | I~~~~~~I | [structure with fluorophenyl benzofuran methylcarboxamide and larger oxa macrocycle] | 396.2 | 396.1 | 2.44 |

| Cmpd # | Di-Electrophile | Structure | MS (M + H)+ Calcd. | MS (M + H)+ Observ. | Retention Time (min) |
|---|---|---|---|---|---|
| 1010 | Br~~~~~~~Br | [macrocyclic benzofuran carboxamide with 4-fluorophenyl and N-methyl amide] | 410.2 | 410.1 | 2.50 |
| 1011 | I~~~~~~~~I | [macrocyclic benzofuran carboxamide with 4-fluorophenyl and N-methyl amide] | 424.2 | 424.1 | 2.57 |
| 1012 | Br~~~~~~~~Br | [macrocyclic benzofuran carboxamide with 4-fluorophenyl and N-methyl amide] | 438.2 | 438.2 | 2.64 |

-continued

| Cmpd # | Di-Electrophile | Structure | MS (M + H)+ Calcd. | MS (M + H)+ Observ. | Retention Time (min) |
|---|---|---|---|---|---|
| 1013 | Br-(CH2)n-Br | 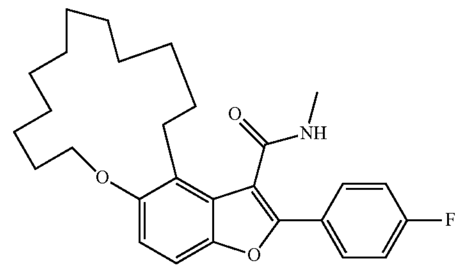 [SMILES: CNC(=O)c1c(-c2ccc(F)cc2)oc2ccc3c(c12)CCCCCCCCCCCCO3] | 452.3 | 452.1 | 2.76 |
| 1014 | 4-methylphenyl-SO2-N(CH2CH2Cl)2 | 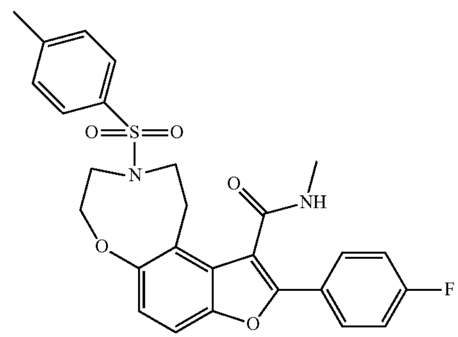 [SMILES: CNC(=O)c1c(-c2ccc(F)cc2)oc2ccc3c(c12)CCN(S(=O)(=O)c1ccc(C)cc1)CCO3] | 509.2 | 509.2 | 2.27 |
| 1015 | BrCH2C(O)NH-CH2CH2-NHC(O)CH2Br | 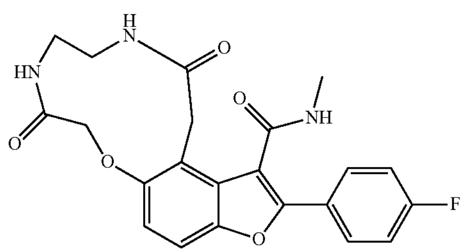 [SMILES: CNC(=O)c1c(-c2ccc(F)cc2)oc2ccc3c(c12)CC(=O)NCCNC(=O)CO3] | 526.1 | 526.2 | 1.55 |

-continued
| Cmpd # | Di-Electrophile | Structure | MS (M + H)+ Calcd. | MS (M + H)+ Observ. | Retention Time (min) |
|---|---|---|---|---|---|
| 2001 | 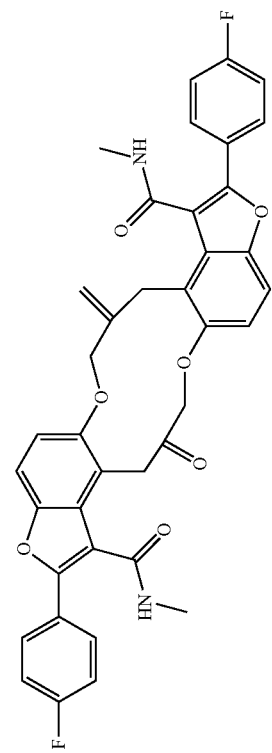 | 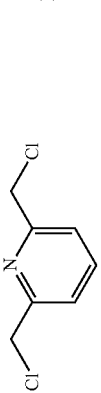 | 777.2 | 777.4 | 2.61 |
| 2002 | 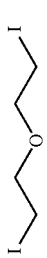 | 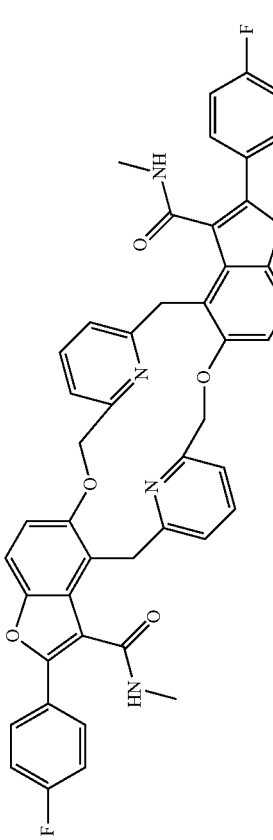 | 675.2 | 675.3 | 2.51 |
| 2003 | 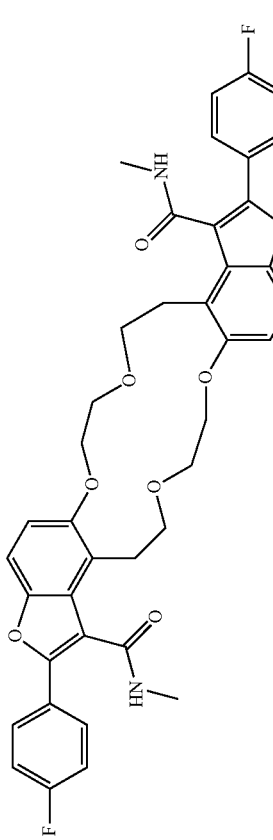 | 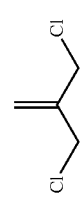 | 711.2 | 711.4 | 2.42 |

-continued

| Cmpd # | Di-Electrophile | Structure | MS (M + H)+ Calcd. | MS (M + H)+ Observ. | Retention Time (min) |
|---|---|---|---|---|---|
| 2004 | [1,3-bis(bromomethyl)benzene] | 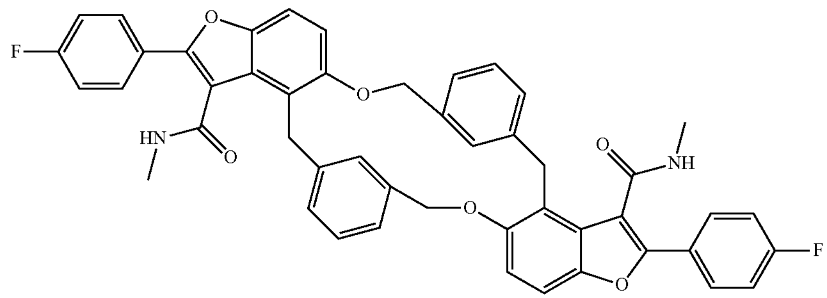 [SMILES: CNC(=O)c1c(-c2ccc(F)cc2)oc2ccc3c(c12)Cc1cccc(c1)COc1ccc2oc(-c4ccc(F)cc4)c(C(=O)NC)c2c1Cc1cccc(c1)CO3] | 775.3 | 775.4 | 2.60 |
| 2005 | [1,1-bis(iodomethyl)cyclopropane] | 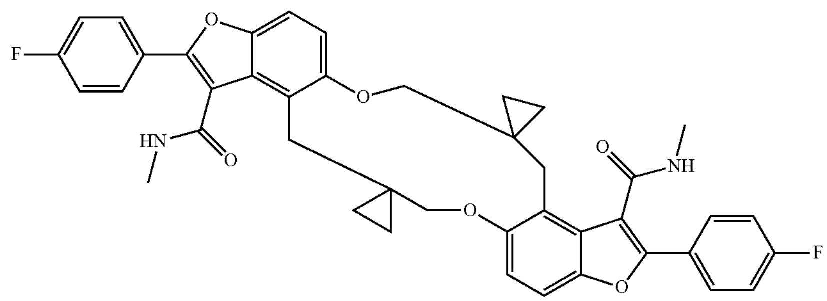 [SMILES: CNC(=O)c1c(-c2ccc(F)cc2)oc2ccc3c(c12)CC1(CC1)COc1ccc2oc(-c4ccc(F)cc4)c(C(=O)NC)c2c1CC1(CC1)CO3] | 703.3 | 703.4 | 2.52 |

Biological Methods

The compound demonstrated activity against HCV NS5B as determined in the following HCV RdRp assays.

HCV NS5B RdRp Cloning, Expression, and Purification.

The cDNA encoding NS5B proteins of HCV genotype 1b (Con1), a genotype 1b variant with amino acid 316 mutated from cysteine to asparagine, and genotype 2a (JFH-1), were cloned into the pET21a expression vector. Each untagged protein was expressed with an 18 amino acid C-terminal truncation to enhance the solubility. The *E. coli* competent cell line BL21(DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 μg/mL and the cells were grown overnight at 20° C.

Cell pellets (3 L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/mL lysozyme, 10 mM $MgCl_2$, 15 ug/mL deoxyribonuclease I, and Complete™ protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 30 minutes at 4° C. and filtered through a 0.2 μm filter unit (Corning).

The protein was purified using two sequential chromatography steps: Heparin sepharose CL-6B and polyU sepharose 4B. The chromatography buffers were identical to the lysis buffer but contained no lysozyme, deoxyribonuclease I, $MgCl_2$ or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

HCV NS5B RdRp enzyme assay. An on-bead solid phase homogeneous assay was used in a 384-well format to assess NS5B inhibitors (WangY-K, Rigat K, Roberts S, and Gao M (2006) Anal Biochem, 359: 106-111). The biotinylated oligo $dT_{12}$ primer was captured on streptavidin-coupled imaging beads (GE, RPNQ0261) by mixing primer and beads in 1× buffer and incubating at room temperature for three hours. Unbound primer was removed after centrifugation. The primer-bound beads were resuspended in 3× reaction mix (20 mM Hepes buffer, pH 7.5, dT primer coupled beads, poly A template, $^3$H-UTP, and RNAse inhibitor (Promega N2515)). Compounds were serially diluted 1:3 in DMSO and aliquoted into assay plates. Equal volumes (5 μL) of water, 3× reaction mix, and enzyme in 3× assay buffer (60 mM Hepes buffer, pH 7.5, 7.5 mM $MgCl_2$, 7.5 mM KCl, 3 mM DTT, 0.03 mg/mL BSA, 6% glycerol) were added to the diluted compound on the assay plate. Final concentration of components in 384-well assay: 0.36 nM template, 15 nM primer, 0.29 μM $^3$H-UTP (0.3 μCi), 1.6 U/μL RNAse inhibitor, 7 nM NS5B enzyme, 0.01 mg/mL BSA, 1 mM DTT, and 0.33 μg/μL beads, 20 mM Hepes buffer, pH 7.5, 2.5 mM $MgCl_2$, 2.5 mM KCl, and 0.1% DMSO.

Reactions were allowed to proceed for 24 hours at 30° C. and terminated by the addition of 50 mM EDTA (5 μL). After incubating for at least 15 minutes, plates were read on an Amersham LEADseeker multimodality imaging system.

$IC_{50}$ values for compounds were determined using ten different [I]. $IC_{50}$ values were calculated from the inhibition using the four-parameter logistic formula $y=A+((B-A)/(1+((C/x)\hat{}D)))$, where A and B denote minimal and maximal % inhibition, respectively, C is the $IC_{50}$, D is hill slope and x represents compound concentration.

Cell Lines. The cell lines used to evaluate compounds consist of a human hepatocyte derived cell line (Huh-7) that constitutively expresses a genotype 1b (Con-1) HCV replicon or a genotype 1b (Con-1) HCV replicon with an asparagine replacing the cysteine at amino acid 316, or a genotype 2a (JFH-1) replicon, containing a *Renilla* luciferase reporter gene. These cells were maintained in Dulbecco's modified Eagle medium (DMEM) containing 10% FBS, 100 U/mL penicillin/streptomycin and 1.0 mg/mL G418.

HCV replicon luciferase assay. To evaluate compound efficacy, titrated compounds were transferred to sterile 384-well tissue culture treated plates, and the plates were seeded with HCV replicon cells (50 μL at a density of 2.4×10$^3$ cells/well) in DMEM containing 4% FBS (final DMSO concentration at 0.5%). After 3 days incubation at 37° C., cells were analyzed for *Renilla* Luciferase activity using the EnduRen substrate (Promega cat #E6485) according to the manufacturer's directions. Briefly, the EnduRen substrate was diluted in DMEM and then added to the plates to a final concentration of 7.5 μM. The plates were incubated for at least 1 hour at 37° C., then read on a Viewlux Imager (PerkinElmer) using a luminescence program. The 50% effective concentration ($EC_{50}$) was calculated using the four-parameter logistic formula noted above.

To assess cytotoxicity of compounds, Cell Titer-Blue (Promega) was added to the EnduRen-containing plates and incubated for at least 4 hrs at 37° C. The fluorescence signal from each well was read using a Viewlux Imager. All $CC_{50}$ values were calculated using the four-parameter logistic formula.

Representative data for compounds are reported in Table 2.

TABLE 2

| Cmpd # | Structure | $EC_{50}$ (uM) 1b |
|---|---|---|
| 1001 | 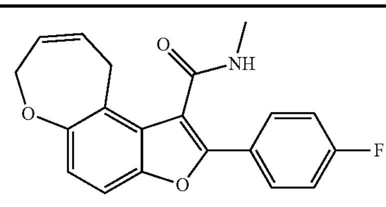 | 2.0790 |

TABLE 2-continued

| Cmpd # | Structure | EC$_{50}$ (uM) 1b |
|---|---|---|
| 1002 | 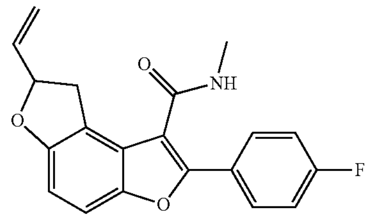 [SMILES: C=CC1Cc2c(ccc3oc(-c4ccc(F)cc4)c(C(=O)NC)c23)O1] | 0.6723 |
| 1003 | 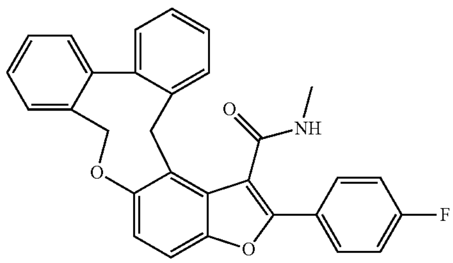 [SMILES: CNC(=O)c1c(-c2ccc(F)cc2)oc2ccc3c(c12)Cc1ccccc1-c1ccccc1CO3] | 2.8440 |
| 1004 | 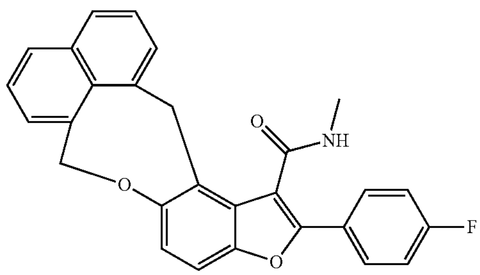 [SMILES: CNC(=O)c1c(-c2ccc(F)cc2)oc2ccc3c(c12)Cc1cccc2cccc(c12)CO3] | >10 |
| 1005 | 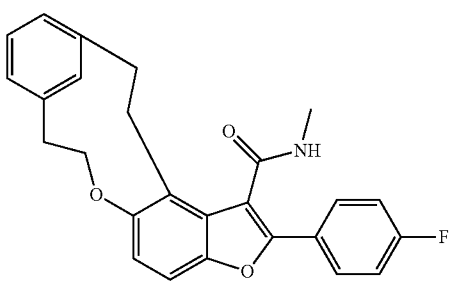 [SMILES: CNC(=O)c1c(-c2ccc(F)cc2)oc2ccc3c(c12)CCc1cccc(c1)CCO3] | >10 |
| 1006 | 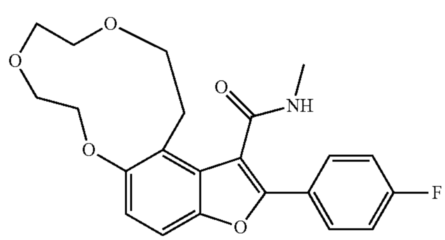 [SMILES: CNC(=O)c1c(-c2ccc(F)cc2)oc2ccc3c(c12)CCOCCOCCO3] | >10 |
| 1007 | 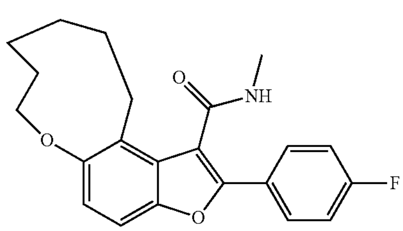 [SMILES: CNC(=O)c1c(-c2ccc(F)cc2)oc2ccc3c(c12)CCCCCCO3] | 1.2880 |

TABLE 2-continued

| Cmpd # | Structure | EC$_{50}$ (uM) 1b |
|---|---|---|
| 1008 | 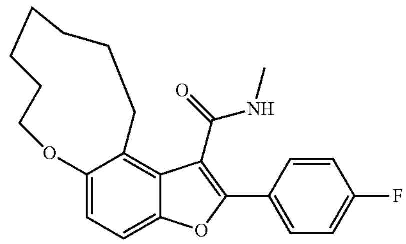 [SMILES: CNC(=O)c1c(-c2ccc(F)cc2)oc2ccc3c(c12)CCCCCCCO3] | 1.8220 |
| 1009 | 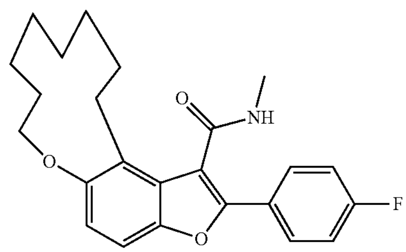 [SMILES: CNC(=O)c1c(-c2ccc(F)cc2)oc2ccc3c(c12)CCCCCCCCO3] | 2.0780 |
| 1010 | 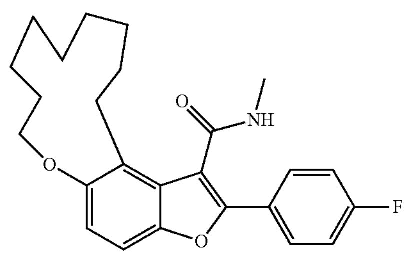 [SMILES: CNC(=O)c1c(-c2ccc(F)cc2)oc2ccc3c(c12)CCCCCCCCCO3] | 1.6270 |
| 1011 | 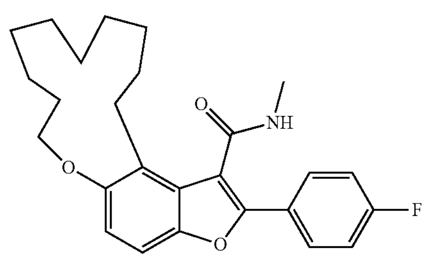 [SMILES: CNC(=O)c1c(-c2ccc(F)cc2)oc2ccc3c(c12)CCCCCCCCCCO3] | 1.0850 |
| 1012 | 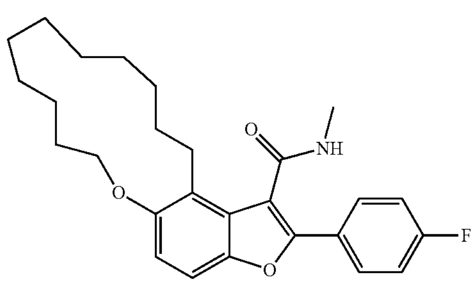 [SMILES: CNC(=O)c1c(-c2ccc(F)cc2)oc2ccc3c(c12)CCCCCCCCCCCO3] | 0.5300 |

TABLE 2-continued

| Cmpd # | Structure | EC$_{50}$ (uM) 1b |
|---|---|---|
| 1013 | 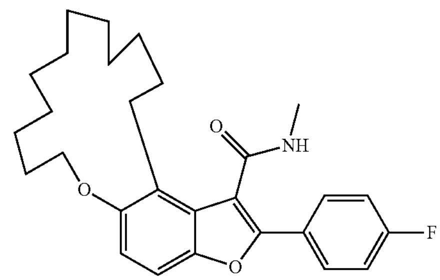 [SMILES: CNC(=O)c1c(-c2ccc(F)cc2)oc2ccc3c(c12)CCCCCCCCCCCCO3] | 1.5130 |
| 1014 | 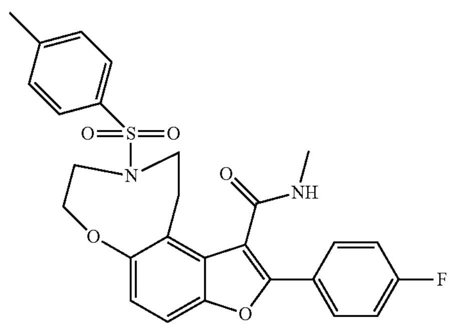 [SMILES: CNC(=O)c1c(-c2ccc(F)cc2)oc2ccc3c(c12)CCN(S(=O)(=O)c1ccc(C)cc1)CCO3] | >10 |
| 1015 | 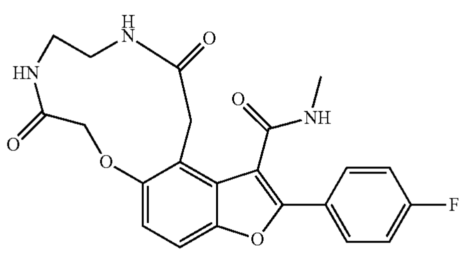 [SMILES: CNC(=O)c1c(-c2ccc(F)cc2)oc2ccc3c(c12)CC(=O)NCCNC(=O)CO3] | >10 |
| 2001 | 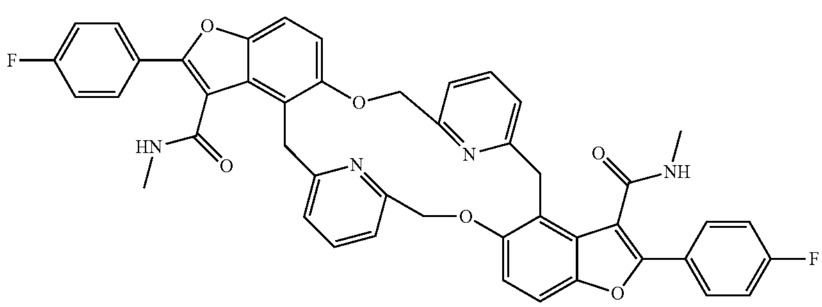 [SMILES: CNC(=O)c1c(-c2ccc(F)cc2)oc2ccc3c(c12)Cc1cccc(n1)COc1ccc2oc(-c4ccc(F)cc4)c(C(=O)NC)c2c1Cc1cccc(n1)CO3] | 6.6720 |
| 2002 | 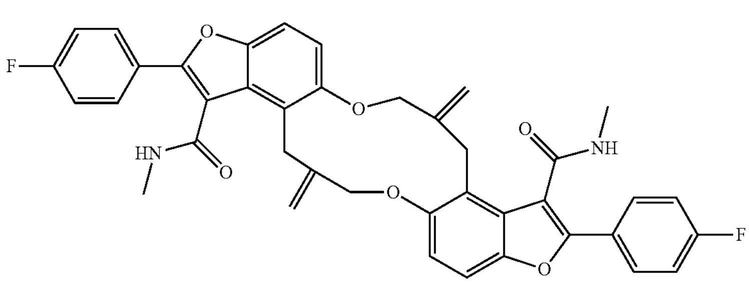 [SMILES: C=C1COc2ccc3oc(-c4ccc(F)cc4)c(C(=O)NC)c3c2CC(=C)COc2ccc3oc(-c4ccc(F)cc4)c(C(=O)NC)c3c2C1] | 3.6510 |

TABLE 2-continued

| Cmpd # | Structure | EC$_{50}$ (uM) 1b |
|---|---|---|
| 2003 | 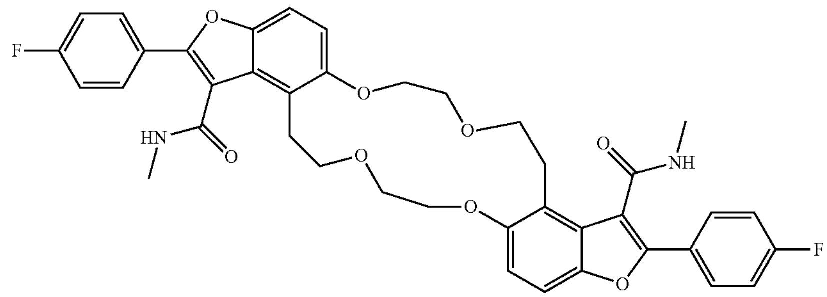 [SMILES: CNC(=O)c1c(-c2ccc(F)cc2)oc2ccc3c(c12)CCOCCOc1ccc2oc(-c4ccc(F)cc4)c(C(=O)NC)c2c1CCOCCO3] | N/A |
| 2004 | 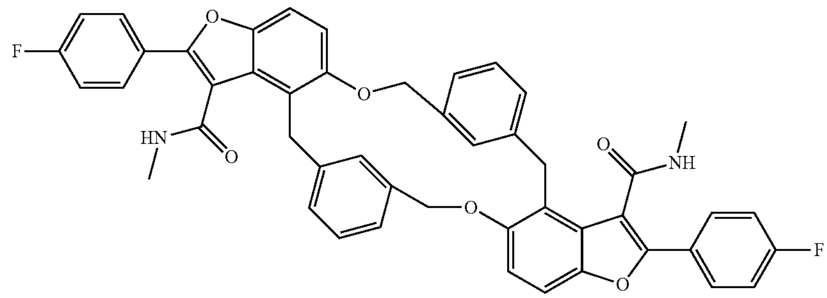 [SMILES: CNC(=O)c1c(-c2ccc(F)cc2)oc2ccc3c(c12)Cc1cccc(c1)COc1ccc2oc(-c4ccc(F)cc4)c(C(=O)NC)c2c1Cc1cccc(c1)CO3] | >10 |
| 2005 | 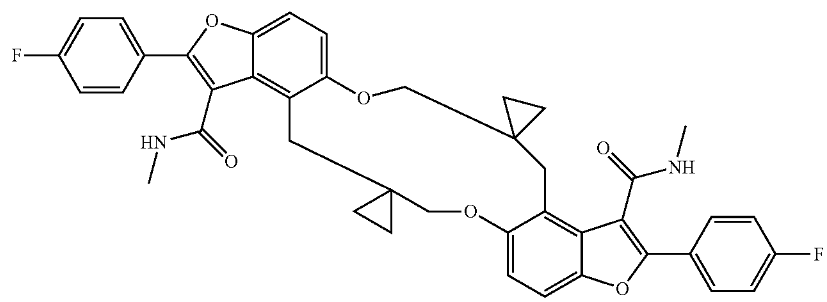 [SMILES: CNC(=O)c1c(-c2ccc(F)cc2)oc2ccc3c(c12)CC1(CC1)COc1ccc2oc(-c4ccc(F)cc4)c(C(=O)NC)c2c1CC1(CC1)CO3] | 0.9308 |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. The compound according to formula I

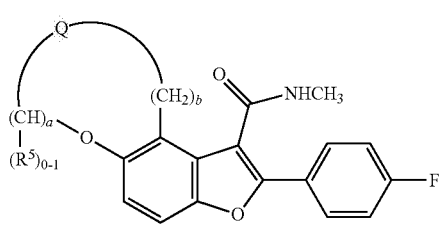

(I)

wherein
a is 1, 2, 3, 4, 5, or 6;
b is 1, 2, 3, 4, 5, or 6;
$R^5$ is $C_1$-$C_3$ alkenyl;
Q is a) -absent;
  b) —CH=CH—;
  c) —(Ar$_1$)$_c$— wherein Ar$_1$ is phenyl, biphenyl or naphthyl and c is 1 or 2;
  d) —(CH$_2$O)$_d$—; wherein d is 1 or 2

   e)

wherein $R^7$ is SO2-optionally substituted aryl;

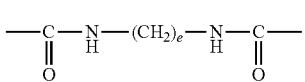   f)

and e is 1,2 or 3;

g) —X₁—(CH₂)_f—Ar₂—(OCH₂)_g—X₂;
  wherein f is 1, 2 or 3, g is 1 or 2 and X₁ and X₂ are independently selected from aryl, —C(=O)—, —O—, or C₃-C₆ cycloalkyl;
Ar₂ is

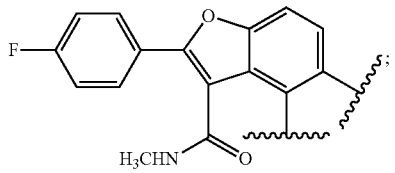

or a pharmaceutically acceptable salt thereof.

2. The compound according to claim 1 wherein
a is 1, 2, 3, 4, 5, or 6;
b is 1, 2, 3, 4, 5, or 6;
R⁵ is —CH=CH₂;
Q is a) -absent;
  b) —CH=CH—;
  c) —(Ar₁)_c— where Ar₁ is phenyl, biphenyl or naphthyl and c is 1 or 2;

d) —(CH₂O)_d—; wherein d is 1 or 2

where R⁷ is SO2-optionally substituted aryl;

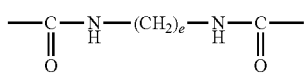

and e is 1, 2 or 3;

g) —X₁—(CH₂)_f—Ar₂—(OCH₂)_g—X₂;
  wherein f is 1, 2 or 3, g is 1 or 2 and X₁ and X₂ are independently selected from aryl, —C(=O)—, —O—, or cyclopropyl;
Ar₂ is

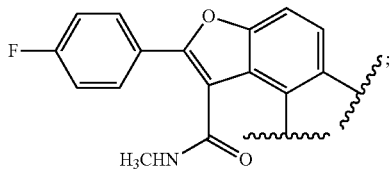

or a pharmaceutically acceptable salt thereof.

3. A compound of claim 1, including a pharmaceutically acceptable salt thereof, selected from the group consisting of

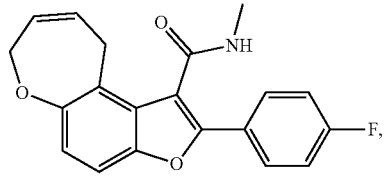

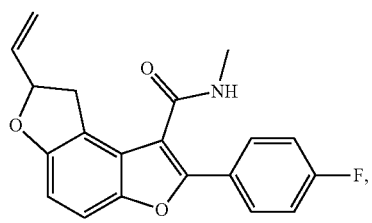

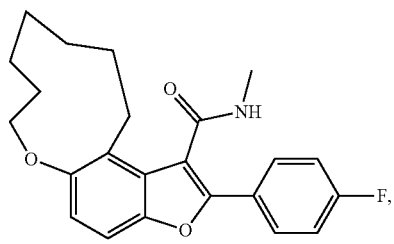

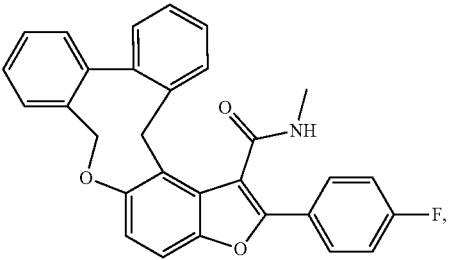

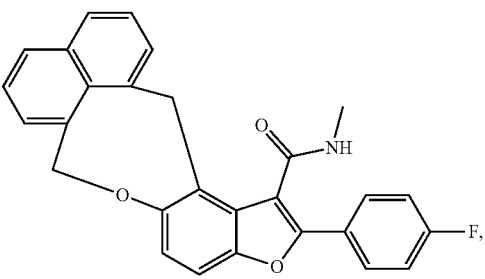

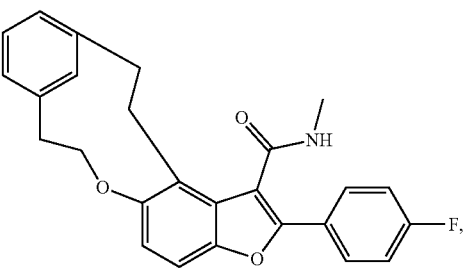

-continued
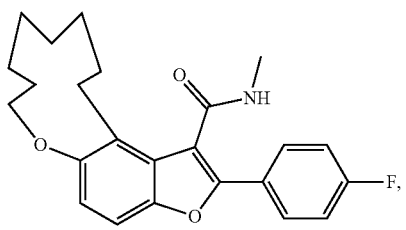
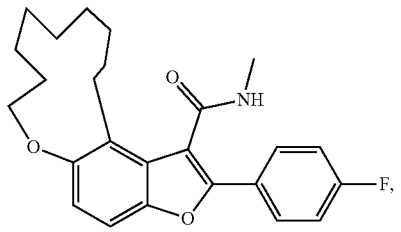
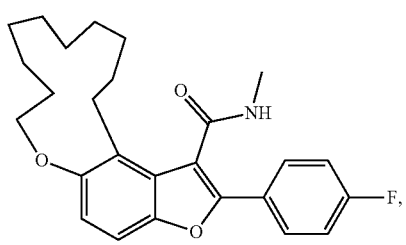
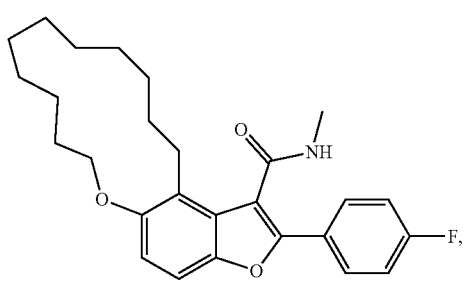
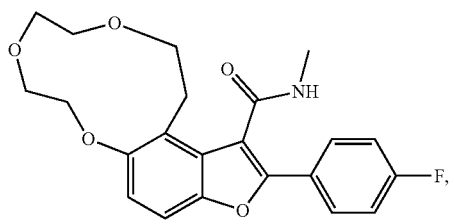
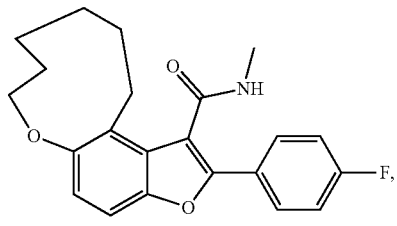
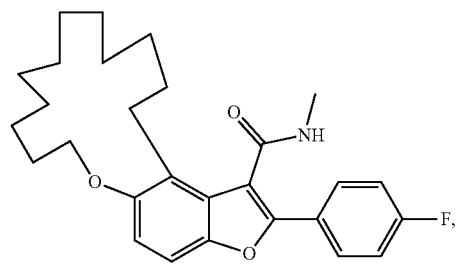
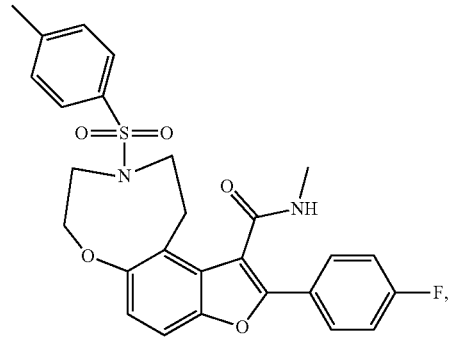
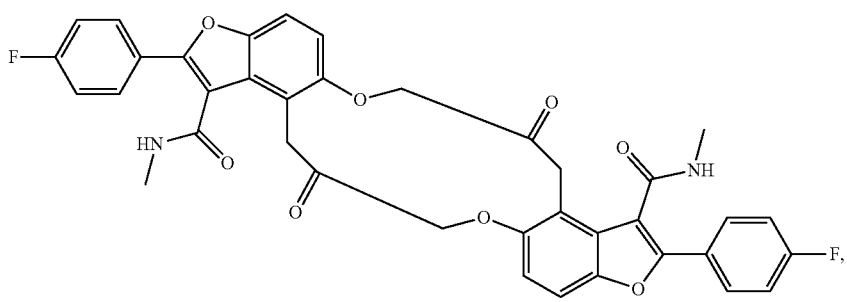
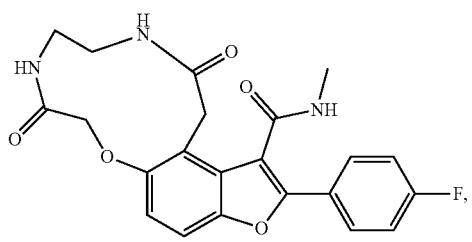

-continued
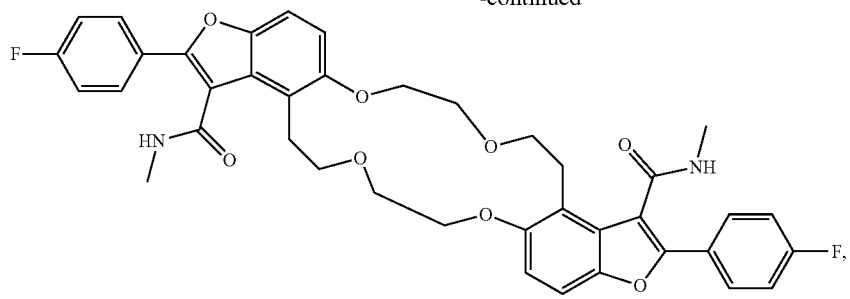
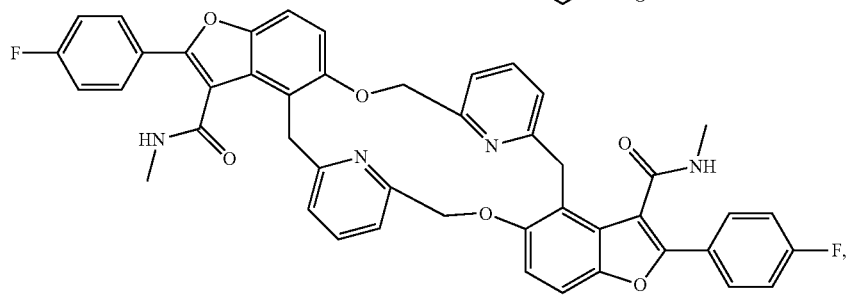
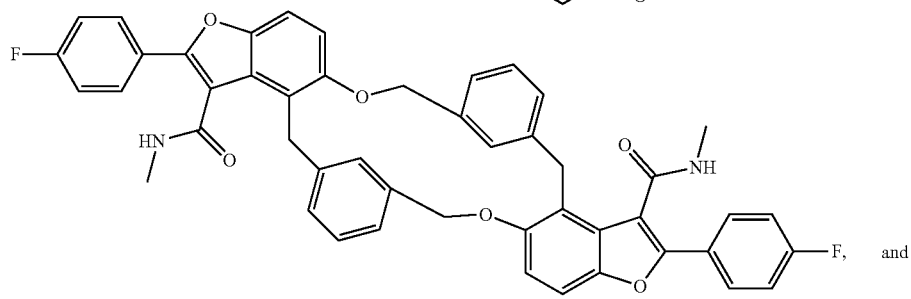
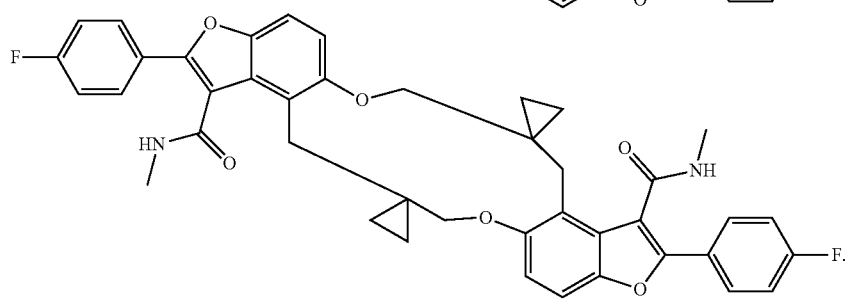
and
4. A pharmaceutical composition comprising a compound of claim 1 or a pharmaceutically acceptable salt thereof and a pharmaceutically acceptable carrier.
5. A compound of claim 1 selected from the group consisting of
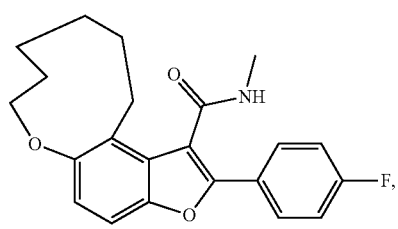
-continued
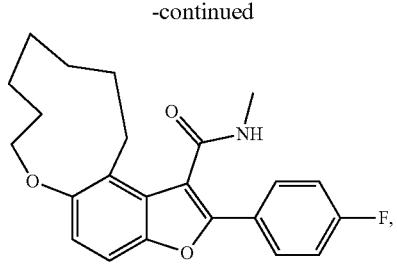
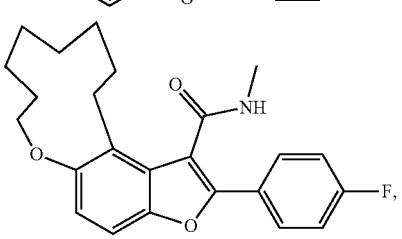

49
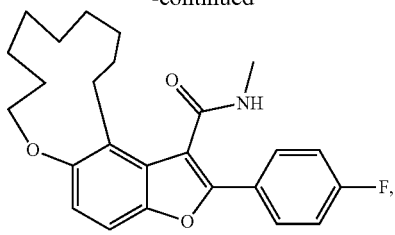
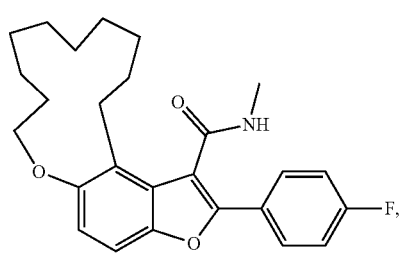
50
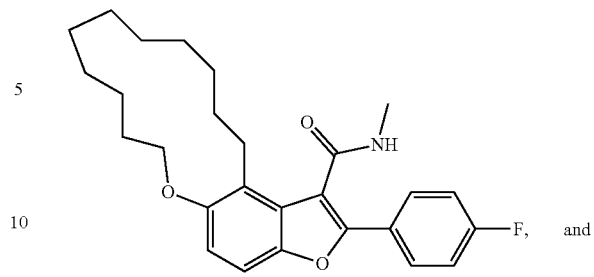
or a pharmaceutically acceptable salt thereof.
* * * * *